United States Patent
Teixeira et al.

(10) Patent No.: US 12,070,350 B2
(45) Date of Patent: Aug. 27, 2024

(54) DETERMINING CT SCAN PARAMETERS BASED ON MACHINE LEARNING

(71) Applicant: Siemens Healthcare AG, Forchheim (DE)

(72) Inventors: Brian Teixeira, Lawrence Township, NJ (US); Vivek Singh, Princeton, NJ (US); Ankur Kapoor, Plainsboro, NJ (US); Andreas Prokein, Bubenreuth (DE); Dorin Comaniciu, Princeton, NJ (US)

(73) Assignee: Siemens Healthineers AG, Forchheim (DE)

( * ) Notice: Subject to any disclaimer, the term of this patent is extended or adjusted under 35 U.S.C. 154(b) by 299 days.

(21) Appl. No.: 17/657,181

(22) Filed: Mar. 30, 2022

(65) Prior Publication Data

US 2022/0346742 A1 Nov. 3, 2022

(30) Foreign Application Priority Data

Apr. 29, 2021 (EP) .................................... 21171208

(51) Int. Cl.
*A61B 6/00* (2006.01)
*A61B 6/03* (2006.01)

(52) U.S. Cl.
CPC .............. *A61B 6/545* (2013.01); *A61B 6/032* (2013.01)

(58) Field of Classification Search
CPC ................................ A61B 6/545; A61B 6/032
See application file for complete search history.

(56) References Cited

U.S. PATENT DOCUMENTS

| 10,475,538 | B2 | 11/2019 | Wu et al. |
| 2018/0049714 | A1 | 2/2018 | Nett |
| 2019/0057521 | A1 | 2/2019 | Teixeira |
| 2020/0000425 | A1 | 1/2020 | Ji et al. |
| 2021/0307715 | A1 | 10/2021 | Krauss |

FOREIGN PATENT DOCUMENTS

CN 110692107 A * 1/2020 ........... G06K 9/6232

OTHER PUBLICATIONS

European Search Report for European Application No. 21171208.8-1126 mailed Nov. 8, 2021.
Park, Jeong Joon, Peter Florence, Julian Straub, Richard Newcombe, and Steven Lovegrove. "Deepsdf: Learning continuous signed distance functions for shape representation." In Proceedings of the IEEE/CVF Conference on Computer Vision and Pattern Recognition, pp. 165-174. 2019.
Trevor Hastie, Robert Tibshirani, Jerome Friedman: "Data Mining, Inference, and Prediction", Jan. 1, 2009 (Jan. 1, 2009), Springer, New York, NY, XP002804458, ISBN: 978-0-387-84857-0, pp. 558-560, (p. 559, equation 14.80).
U.S. Appl. No. 17/489,838, filed Sep. 30, 2021.

* cited by examiner

*Primary Examiner* — David P Porta
*Assistant Examiner* — Fani Polyzos Boosalis

(57) ABSTRACT

CT scan parameters for performing a CT scan of an anatomical target region of a patient are determined and/or adjusted. An initial set of the CT scan parameters for starting to perform the CT scan is determined based on an initial set of attenuation curves associated with the anatomical target region of the patient. The initial set of attenuation curves are determined based on optical imaging data depicting the patient.

18 Claims, 7 Drawing Sheets

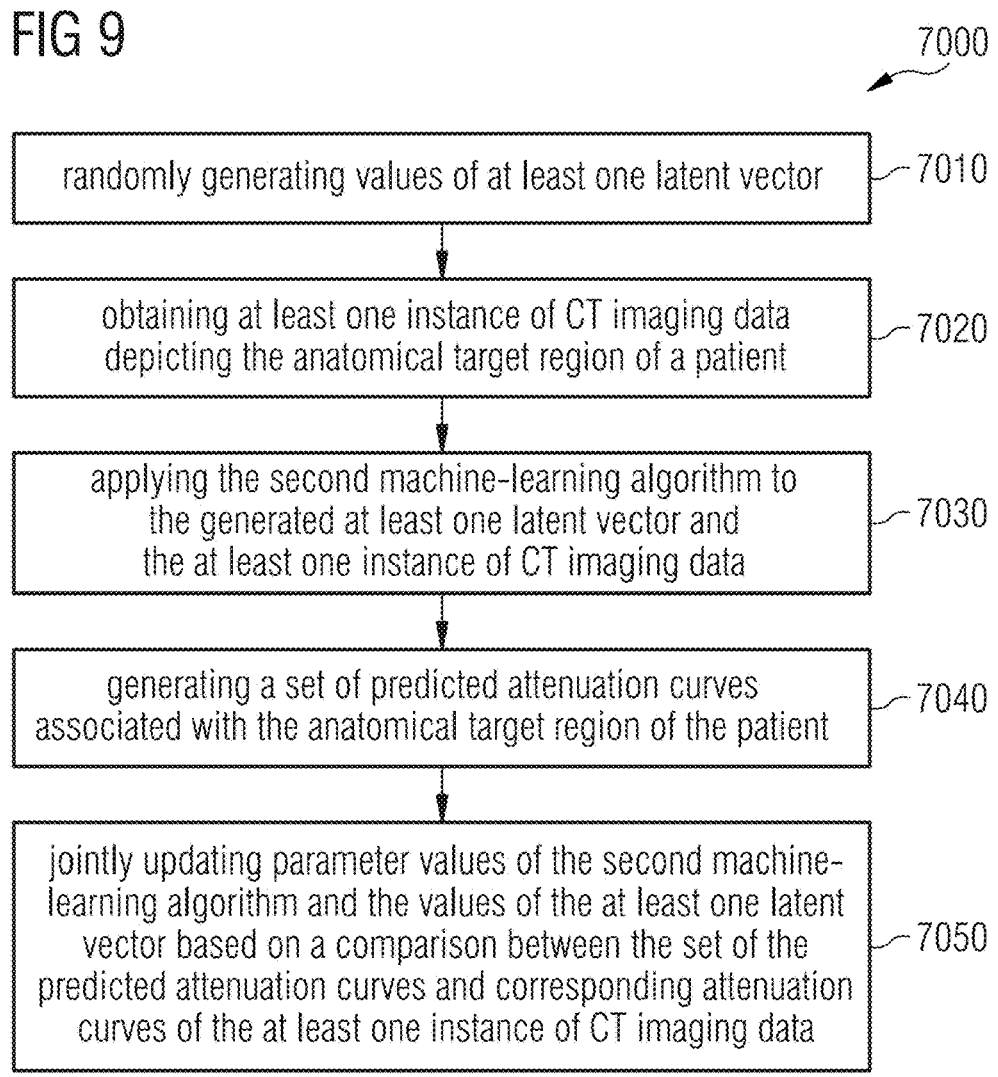
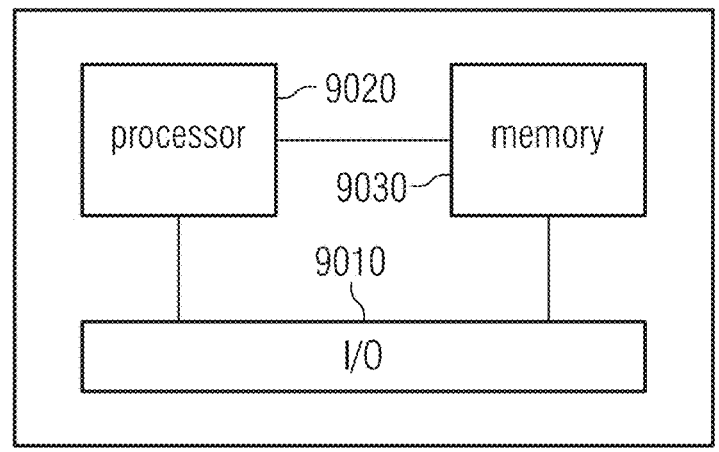

DETERMINING CT SCAN PARAMETERS BASED ON MACHINE LEARNING

This application claims the benefit of EP 21171208.8, filed Apr. 29, 2021, which is hereby incorporated by reference in its entirety.

TECHNICAL FIELD

Various examples of the disclosure relate to determining/adjusting computed tomography (CT) scan parameters for performing a CT scan. Various examples of the disclosure specifically relate to determining, by a first and second machine-learning algorithm, an initial set of attenuation curves associated with an anatomical target region of a patient based on optical imaging data and determining an initial set of the CT scan parameters based on the initial set of attenuation curves.

BACKGROUND

Recent technologic advances have dramatically augmented the clinical applications of CT. While the benefits of CT exceed the harmful effects of radiation exposure in most patients, concern has been raised on the dose of increased utilization of CT procedures and the stochastic effects to the population. Several studies have found that to maintain constant image noise, CT dose increases approximately exponentially with patient body size. Thus, determination of patient body size plays an important role in the proper management of CT radiation dose.

One approach to estimate the patient body size, x-ray attenuation properties related to the patient body etc. is using topograms acquired prior to CT scan. FIG. 1 schematically illustrates an exemplary topogram from pulmonary CT examination. The topograms (aka scouts, purviews, or scanograms) are the scanned projection radiographic images used in CT to prescribe the scan range 1101, x-ray attenuation properties of an anatomical target region (e.g., the lung) located in the scan range 1101 and so on. The orthogonal-view topograms 1102 and 1103 are acquired anterior-posteriorly and laterally with respect to the patient 1104 and are thus referred to as AP 1102 and lateral 1103 topograms, respectively. Individual x-ray attenuation properties of an anatomical target region of the patient 1104 can be derived from the topograms 1102 and 1103, such as a set of attenuation curves (e.g., 1105-*a* corresponding to line 1107-*a*) depicting x-ray attenuation properties of the anatomical structures along a line (e.g., 1107-*a*, 1107-*b*, 1107-*c*) crossing the scan range. Thereby, CT scan parameters, especially radiation-dose-related parameters, such as tube current and tube potential/voltage of an x-ray tube 1106, can be determined/adjusted based on the individual x-ray attenuation properties.

However, such techniques face certain restrictions and drawbacks. For instance, acquiring topograms expose patients to radiation. Acquiring topograms is typically time-consuming.

SUMMARY

Accordingly, there is a need for advanced techniques that mitigate or overcome the above-identified drawbacks or restrictions. There is a need for advances techniques of determining CT scan parameters.

This need is met by the features of the current embodiments.

Hereinafter, techniques of determining and/or adjusting CT scan parameters for performing a CT scan will be described. An initial set of attenuation curves associated with an anatomical target region of a patient may be determined, by a first and second machine-learning algorithm, based on optical imaging data depicting the patient, and then an initial set of the CT scan parameters may be determined based on the initial set of attenuation curves.

A computer-implemented method is provided. The method is used to determine computed tomography (CT) scan parameters for performing a CT scan of an anatomical target region of a patient. The method includes determining, based on optical imaging data depicting the patient, an initial set of attenuation curves. The initial set of attenuation curves is associated with the anatomical target region of the patient. The method further includes determining an initial set of the CT scan parameters based on the initial set of attenuation curves and performing the CT scan starting with the initial set of the CT scan parameters.

A computer program, a computer-program product, or a non-transitory computer-readable storage medium that includes program code is provided. The program code can be loaded and executed by at least one processor. Upon loading and executing the program code, the at least one processor performs a method. The method is used to determine computed tomography (CT) scan parameters for performing a CT scan of an anatomical target region of a patient. The method includes determining, based on optical imaging data depicting the patient, an initial set of attenuation curves. The initial set of attenuation curves is associated with the anatomical target region of the patient. The method further includes determining an initial set of the CT scan parameters based on the initial set of attenuation curves and performing the CT scan starting with the initial set of the CT scan parameters.

A computer-implemented method is provided. The method is used to perform a first training of a first machine-learning algorithm. The first machine-learning algorithm is configured to determine computed tomography (CT) scan parameters for performing a CT scan of an anatomical target region. The method includes generating, by the first machine-learning algorithm and based on multiple instances of training optical imaging data depicting a patient, at least one latent vector. The at least one latent vector represents the multiple instances of the training optical imaging data. The method further includes generating, by a second trained machine-learning algorithm, a set of predicted attenuation curves associated with the anatomical target region of the patient based on the generated at least one latent vector and at least one instance of CT imaging data depicting the anatomical target region of the patient. The method further includes updating parameter values of the first machine-learning algorithm based on a comparison between the set of the predicted attenuation curves and corresponding attenuation curves of the at least one instance of CT imaging data.

A computer program, a computer-program product, or a non-transitory computer-readable storage medium that includes program code is provided. The program code can be loaded and executed by at least one processor. Upon loading and executing the program code, the at least one processor performs a method. The method is used to perform a first training of a first machine-learning algorithm. The first machine-learning algorithm is configured to determine computed tomography (CT) scan parameters for performing a CT scan of an anatomical target region. The method includes generating, by the first machine-learning algorithm and based on multiple instances of training optical imaging data depicting a patient, at least one latent vector. The at least one latent vector represents the multiple instances of the training optical imaging data. The method further includes generating, by a second trained machine-learning algorithm, a set of predicted attenuation curves associated with the anatomical target region of the patient based on the generated at least one latent vector and at least one instance of CT imaging data depicting the anatomical target region of the patient. The method further includes updating parameter values of the first machine-learning algorithm based on a comparison between the set of the predicted attenuation curves and corresponding attenuation curves of the at least one instance of CT imaging data.

A computer-implemented method is provided. The method is used to perform a second training of a second machine-learning algorithm. The second machine-learning algorithm is configured to determine computed tomography (CT) scan parameters for performing a CT scan of an anatomical target region. The method includes randomly generating values of at least one latent vector. The method further includes obtaining at least one instance of CT imaging data depicting the anatomical target region of a patient. The method further includes applying the second machine-learning algorithm to the generated at least one latent vector and the at least one instance of CT imaging data. The method further includes generating a set of predicted attenuation curves associated with the anatomical target region of the patient. The method further includes jointly updating parameter values of the second machine-learning algorithm and the values of the at least one latent vector based on a comparison between the set of the predicted attenuation curves and corresponding attenuation curves of the at least one instance of CT imaging data.

A computer program, a computer-program product, or a non-transitory computer-readable storage medium that includes program code is provided. The program code can be loaded and executed by at least one processor. Upon loading and executing the program code, the at least one processor performs a method. The method is used to perform a second training of a second machine-learning algorithm. The second machine-learning algorithm is configured to determine computed tomography (CT) scan parameters for performing a CT scan of an anatomical target region. The method includes randomly generating values of at least one latent vector. The method further includes obtaining at least one instance of CT imaging data depicting the anatomical target region of a patient. The method further includes applying the second machine-learning algorithm to the generated at least one latent vector and the at least one instance of CT imaging data. The method further includes generating a set of predicted attenuation curves associated with the anatomical target region of the patient. The method further includes jointly updating parameter values of the second machine-learning algorithm and the values of the at least one latent vector based on a comparison between the set of the predicted attenuation curves and corresponding attenuation curves of the at least one instance of CT imaging data.

A system including at least one processor and at least one memory is provided. The at least one processor is configured to load program code from the at least one memory and execute the program code. Upon executing the program code, the at least one processor is configured to train the first and second machine-learning algorithm. The first and second machine-learning algorithms are configured to determine computed tomography (CT) scan parameters for performing a CT scan of an anatomical target region. The second machine-learning algorithm is trained. The processor is configured to apply the second machine-learning algorithm to randomly generated values of at least one latent vector and the at least one instance of CT imaging data. The processor is further configured to generate a set of predicted attenuation curves associated with the anatomical target region of the patient. The processor is further configured to jointly update parameter values of the second machine-learning algorithm and the values of the at least one latent vector based on a comparison between the set of the predicted attenuation curves and corresponding attenuation curves of the at least one instance of CT imaging data. The processor is configured to train the first machine-learning algorithm. The processor is configured to generate, by the first machine-learning algorithm and based on multiple instances of training optical imaging data depicting a patient, at least one latent vector. The at least one latent vector represents the multiple instances of the training optical imaging data. The processor is configured to generate, by the second trained machine-learning algorithm, a set of predicted attenuation curves associated with the anatomical target region of the patient based on the generated at least one latent vector and at least one instance of CT imaging data depicting the anatomical target region of the patient. The processor is configured to update parameter values of the first machine-learning algorithm based on a comparison between the set of the predicted attenuation curves and corresponding attenuation curves of the at least one instance of CT imaging data.

A computed tomography (CT) scanner is provided. The CT scanner includes at least one optical imaging device. The at least one optical imaging device (camera) is configured to capture optical imaging data depicting a patient. The CT scanner further includes a computing unit (computer or processor). The computing unit is configured to determine computed tomography (CT) scan parameters for performing a CT scan of an anatomical target region of the patient. The computing unit is configured to determine, based on the at least one optical imaging data depicting the patient, an initial set of attenuation curves. The initial set of attenuation curves is associated with the anatomical target region of the patient. The computer is configured to determine an initial set of the CT scan parameters based on the initial set of attenuation curves and perform the CT scan starting with the initial set of the CT scan parameters It is to be understood that the features mentioned above and those yet to be explained below may be used not only in the respective combinations indicated, but also in other combinations or in isolation without departing from the scope of the invention.

BRIEF DESCRIPTION OF THE DRAWINGS

FIG. 9 is a flowchart of a method according to various examples.

FIG. 10 is a block diagram of a system according to various examples.

DETAILED DESCRIPTION OF THE DRAWINGS

Figure 1:
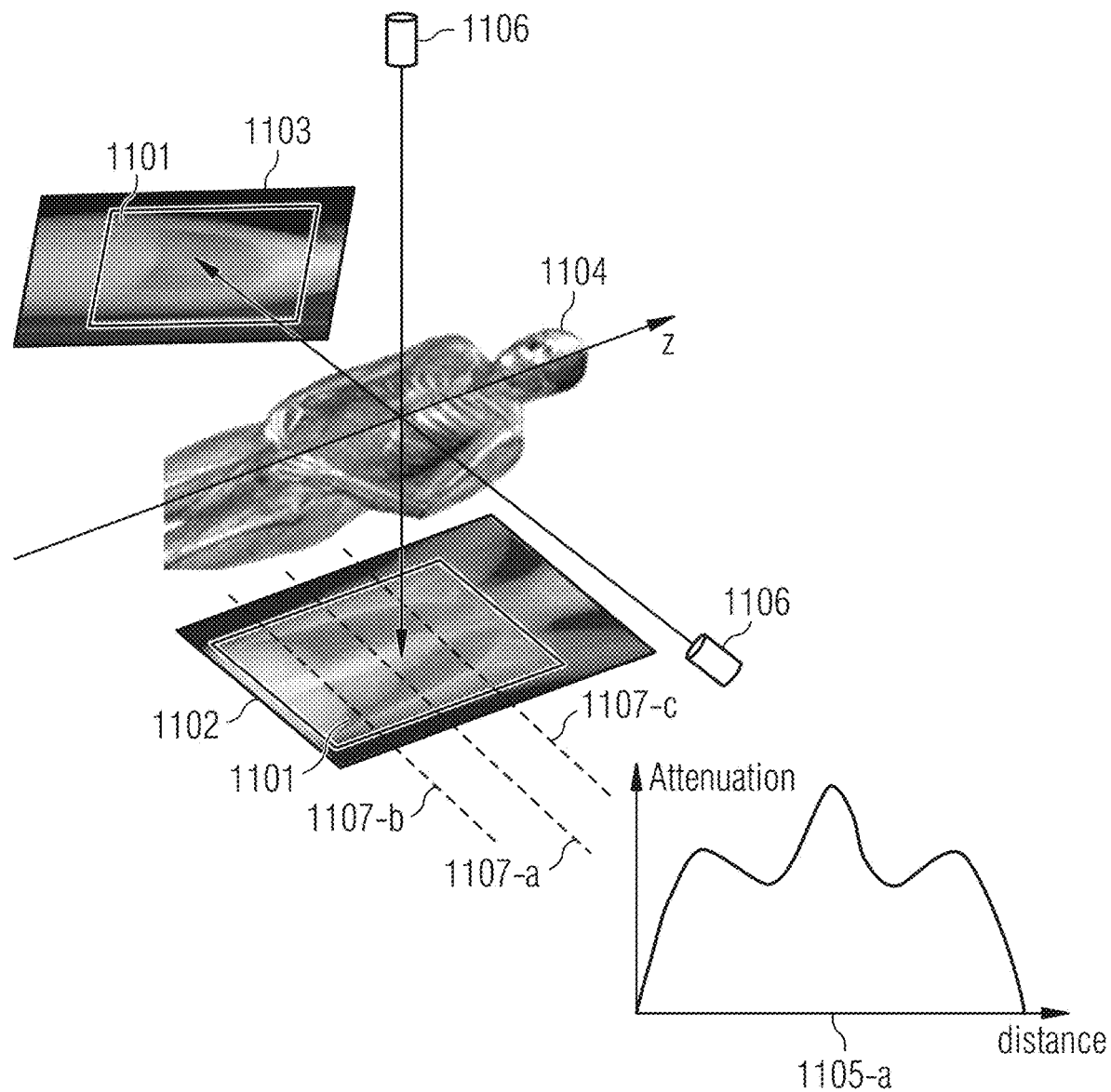
FIG. 1 schematically illustrates an exemplary topograms from pulmonary CT examination.

Some examples of the present disclosure generally provide for a plurality of circuits or other electrical devices. All references to the circuits and other electrical devices and the functionality provided by each are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical implementation that is desired. It is recognized that any circuit or other electrical device disclosed herein may include any number of microcontrollers, a graphics processor unit (GPU), integrated circuits, memory devices (e.g., FLASH, random access memory (RAM), read only memory (ROM), electrically programmable read only memory (EPROM), electrically erasable programmable read only memory (EEPROM), or other suitable variants thereof), and software which co-act with one another to perform operation(s) disclosed herein. In addition, any one or more of the electrical devices may be configured to execute a program code that is embodied in a non-transitory computer readable medium programmed to perform any number of the functions as disclosed.

In the following, embodiments of the invention will be described in detail with reference to the accompanying drawings. It is to be understood that the following description of embodiments is not to be taken in a limiting sense. The scope of the invention is not intended to be limited by the embodiments described hereinafter or by the drawings, which are taken to be illustrative only.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various techniques disclosed herein generally relate to determining CT scan parameters for performing a CT scan. For instance, the CT scan parameters can be determined ab initio, i.e., without prior knowledge. It would be possible that the CT scan parameters are determined by adjusting pre-defined CT scan parameters.

According to various examples, the CT scan parameters are determined based on attenuation curves associated with an anatomical target region of a patient. In particular, an initial set of attenuation curves can be determined based on optical imaging data depicting the patient and thereby an initial set of the CT scan parameters is determined as well. Alternatively, the CT scan parameters or the initial set of the CT scan parameters may be directly determined based on the optical imaging data by using machine-learning technologies, i.e., without relying on the attenuation curves in an intermediate act.

According to the disclosure, various CT scan parameters may be determined automatically or by radiologists. This may help to reduce patient radiation dose, while designing or altering scan protocols. As shown in Table 1, such CT scan parameters may include at least one of scan range, detector configuration, tube current, tube current, patient positioning, reconstructed slice thickness, or pitch.

TABLE 1 various CT scan parameters

| CT scan parameter | description |
|---|---|
| scan range | |
| detector configuration | Detector configuration is a term encompassing the number of data channels being used in the z axis and the "effective detector thickness" of each data channel. For example, a detector configuration of 64 × 0.5 mm would suggest the use of 64 data channels in the z-axis, each of which has an effective thickness of 0.5 mm. Notably, the effective detector thickness represents the smallest possible reconstructed slice thickness. Both the number of channels used and the effective detector thickness can be varied depending on how many channels in a detector array are used, which channels in a detector array are used, and the manner in which different channels are combined. Different scanners from different manufacturers have different included detector channels, and the detector configurations available on different equipment can vary widely. |
| tube current | Tube current depicts the current of the x-ray tube of a CT scanner. Increases in tube current or the product of tube current and scan time (mAs) result in improved image quality, decreased image noise, and increased patient dose. In general, the relationship between tube current and patient dose is essentially linear, with increases in mAs resulting in a comparable percentage increase in patient dose. Although tube current can be manually controlled, most operators use automated tube current modulation (also known as automated exposure control) for most applications. The automated tube current modulation automatically increases the mAs in those parts of the body with the greatest attenuation and decreases the mAs in those parts of the body with lower attenuation. |
| tube potential | Tube potential may be defined as the electrical "potential" difference between anode and cathode of the x-ray tube of CT scanners. Reducing the tube potential can be an effective way of reducing the radiation dose imparted during an examination. As a general rule of thumb, the radiation dose changes with the square of the tube potential, and a reduction in the tube potential from 120 Kilovoltage peak (kVp) to 100 kVp reduces radiation dose by 33%, while a further reduction to 80 kVp can reduce dose by 65%. |
| patient positioning | Proper patient positioning can be defined as choosing the ideal CT table height at which the scanner isocenter coincides with the patient's isocenter. Patient positioning affects the patient's shape and size on a CT localizer radiograph, directly affecting automated tube current modulation behavior as well as the efficacy of bowtie filters. Improper patient positioning has a significant impact on both image noise and patient surface dose. |
| reconstructed slice thickness | Reconstructed slice thickness controls the spatial resolution in the longitudinal direction, influencing the tradeoffs among resolution, noise, and radiation dose. As the reconstructed slice thickness decreases, the number of photons within each voxel also decreases, resulting in increased image noise. To maintain constant noise levels within an image with a smaller slice thickness, the radiation dose must be |

TABLE 1-continued various CT scan parameters

| CT scan parameter | description |
|---|---|
| | consequently increased. |
| pitch | Pitch in the multidetector, spiral CT era is defined as table travel per rotation divided by beam collimation. Pitch < 1 suggests overlap between adjacent acquisitions, pitch > 1 implies gaps between adjacent acquisitions, and pitch of 1 suggests that acquisitions are contiguous, with neither overlap nor gaps. A smaller pitch, with increased overlap of anatomy and increased sampling at each location, results in an increased radiation dose. Alternatively, a larger pitch implies gaps in the anatomy and hence lower radiation dose. |

According to the disclosure, at least one of the following attenuation curves may be determined based on optical imaging data. Mean AP attenuation curve, representing the mean body density averaged on the Anterior Posterior (AP) orthographic projection, Max AP attenuation curve, representing the maximum body density averaged on the AP orthographic projection, and Max lateral attenuation curve, representing the maximum body density averaged on the lateral orthographic projection.

As a general rule, the attenuation curves may be regarded as 1-D continuous or discrete signals and thereby may be represented by vectors. A set of attenuation curves may be represented by a matrix.

According to the disclosure, the anatomical target region may include at least one of head, lung, heart, chest, abdomen, leg, arm, and etc.

According to the disclosure, one or multiple non-ionizing sensors may be used to acquire optical imaging data depicting the patient. For instance, it would be possible that a method for determining CT scan parameters includes controlling the one or more non-ionizing sensors to acquire the optical imaging data.

According to various examples, the optical imaging data can be acquired using a sensor that detects electromagnetic waves in a certain wavelength. For instance, the electromagnetic waves may have wavelengths in the range of 1800 nanometers to 300 nanometers. Respective photons may not traverse tissue of the patient; hence, the optical imaging data may depict the outer surface of the patient. As a general rule, active or passive illumination would be possible. Ranging measurements would be possible.

Non-ionizing sensors may be used for acquiring the optical imaging data; e.g., a Time of Flight (ToF) depth sensor (e.g., Microsoft Kinect or ASUS Xtio), a LiDAR camera (e.g., Intel RealSense L515) or a regular RGB camera. The depth sensor may be a camera or cameras capturing a grid projected onto the patient. Multiple cameras may reconstruct an outer surface from multiple images without transmission of structured light.

By using the optical imaging data, fast imaging without exposing the patient to ionizing radiation becomes possible. The attenuation curves can be determined fast and reliably.

The optical sensor may be directed at a patient. The sensor may capture the outer surface of the patient from one or more perspectives. Multi-perspective optical imaging data could be acquired. Any portion of the outer surface may be captured, such as the entire patient from head to toe and hand to hand on one side or just the torso.

The outer surface may be the skin of the patient. Optionally or alternatively, the outer surface may include clothing. The sensor may use a frequency that passes through clothing and detects skin surface.

The outer surface may be captured as depths from the sensor to different locations on the patient, such as optical imaging data including an image or photograph of the outside of the patient, or both. The sensor may output the optical imaging data including images and/or depths. Alternatively, the optical imaging data may be processed to determine the outer surface of the patient, such as stereoscopically determining the outer surface from camera images from different angles with image processing and may thereby determine measurements of the outer surface.

The measurements of the outer surface may be used to determine a statistical shape model that is fit to the depths. The statistical shape model may be a mesh or other representation of an average or other statistical representation of an outside of a human or part of a human. The statistical shape model may include probabilities or other constraints on alteration, so that the fitting maintains the shape based on statistics.

According to the disclosure, the one or multiple non-ionizing sensors may be mounted on a gantry of a CT scanner, or on a framework matching the gantry of the CT scanner such that the optical imaging data may be acquired when the patient lay down on the patient table of the CT scanner. Before capturing the optical imaging data, the height of the patient table may be determined/adjusted so that the CT scanner isocenter coincides with the patient's isocenter.

Figure 2:
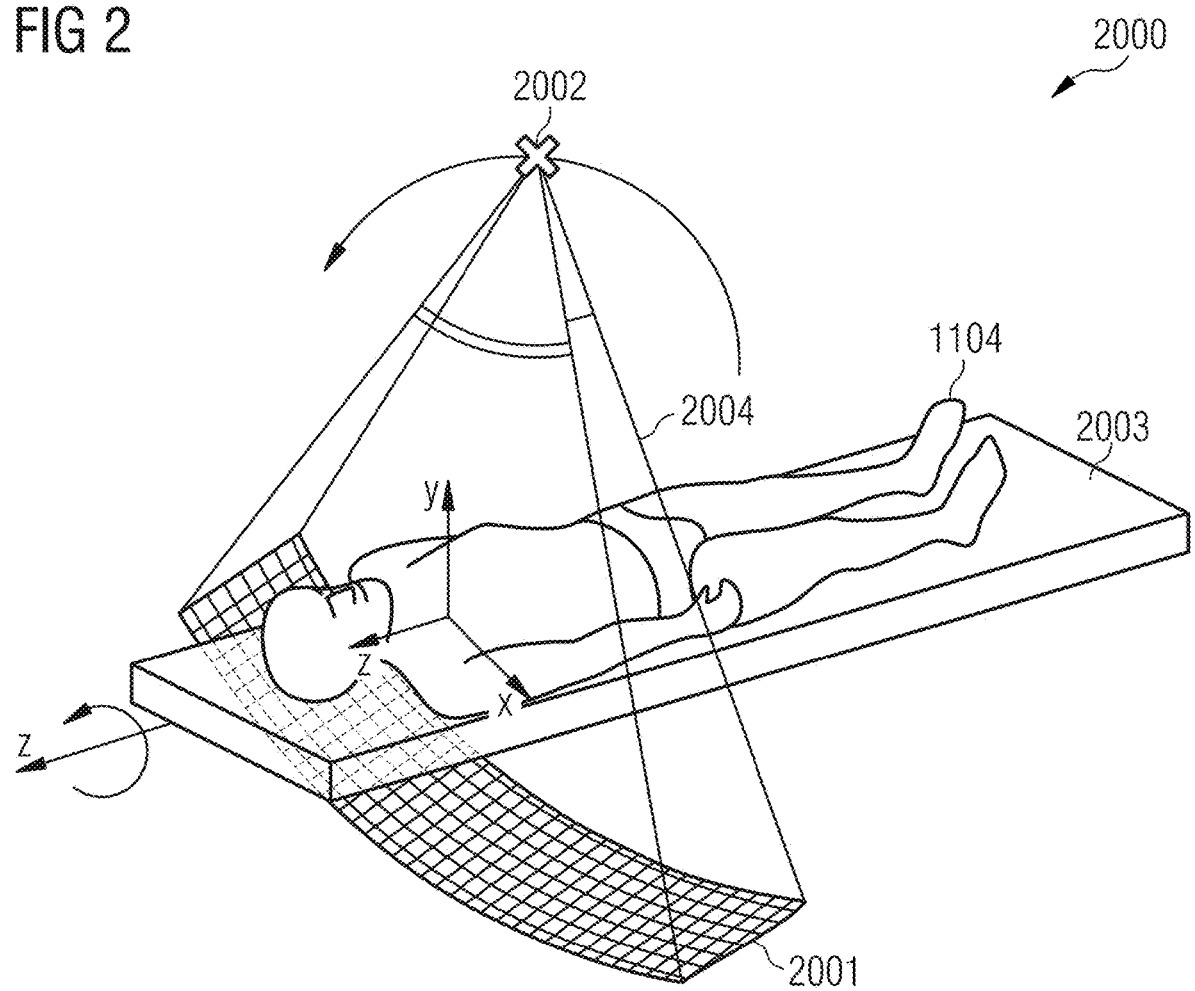
FIG. 2 schematically illustrates an exemplary geometry of a CT scanner.

FIG. 2 schematically illustrates an exemplary geometry of a CT scanner 2000. The CT scanner 2000 includes an x-ray tube 2002, a detector array 2001, a patient table 2003. The x-ray tube 2002 may be a cone-beam x-ray tube emitting an x-ray beam 2004 divergent in and covering an appreciable extent in the longitudinal (z) direction. The detector array 2001 may be a curved detector array having multiple rows of detectors. Both the x-ray tube 2002 and the detector array 2001 may be mounted on a C-arm, U-arm, or O-arm gantry depending on clinical applications ranging from image-guided interventions to diagnostic specialties. The CT scanner 2000 may operate with the patient 1104 stationary on the patient table 2003, and the x-ray tube 2002 together with the detector array 2001 rotate once to acquire a volumetric image. Alternatively, or optionally, the CT scanner 2000 may operate using helical acquisition—with exquisitely engineered patient table 2003 for longitudinal (z-direction) translation of the patient during the scan.

According to the disclosure, a new workflow for performing a CT of an anatomical target region of a patient is provided. The new workflow utilizes optical imaging data acquired by one or multiple non-ionizing sensors as outlined above to determine an initial set of the CT scan parameters to control elements of the CT scanner 2000, such as a height of the patient table 2003, a tube current and a tube potential of the x-ray tube 2002, a configuration of the detector array 2001, etc., and thereby start the CT scan. The optical imaging data can render topograms unnecessary to determine the initial set of the CT scan parameters, which accordingly eliminates patient radiation caused by acquiring topograms prior to CT scan.

Figure 3:
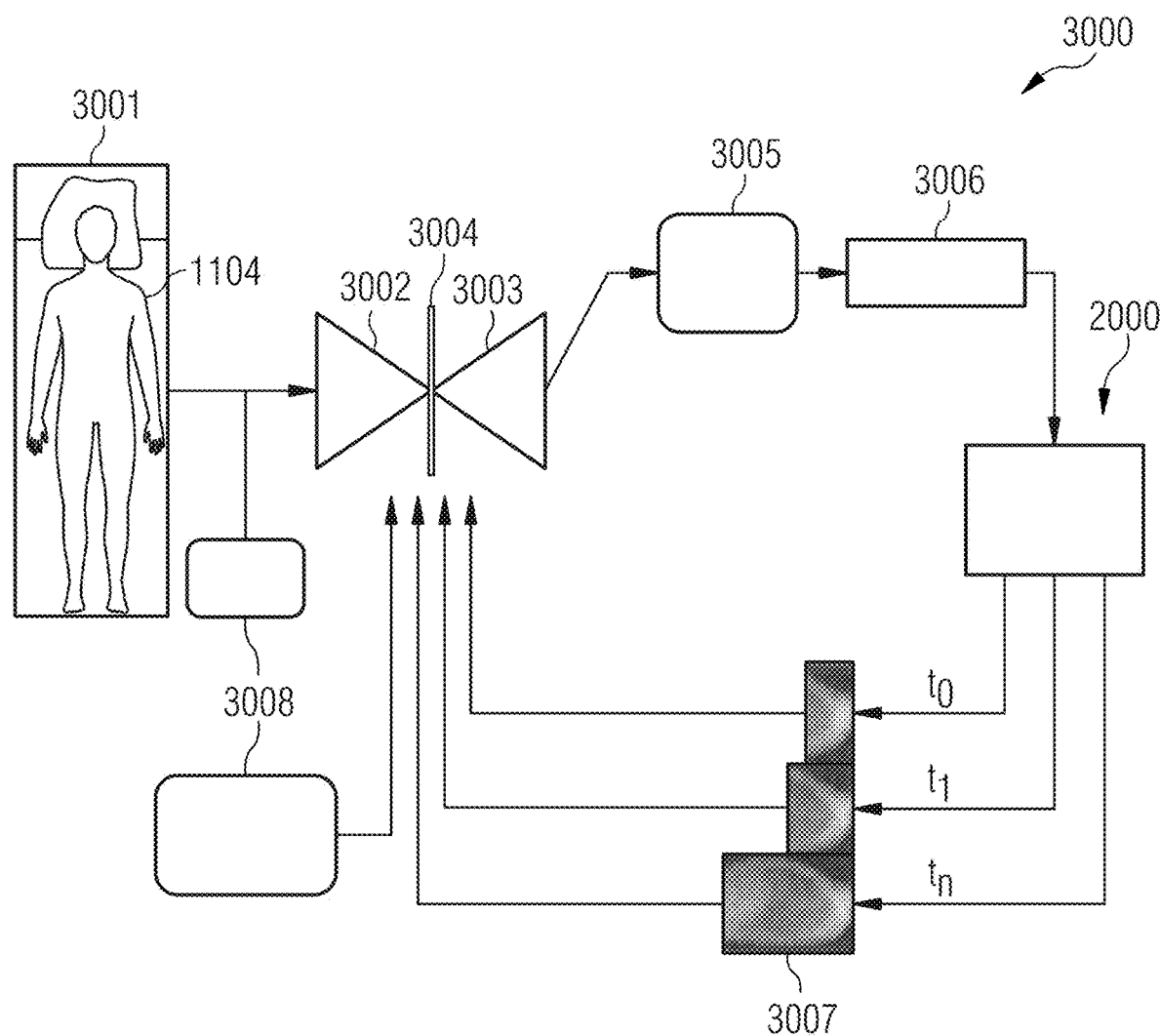
FIG. 3 schematically illustrates details with respect to a system according to various examples.

FIG. 3 schematically illustrates details with respect to a system 3000 according to various examples. The system 3000 pertains to determining CT scan parameters for performing a CT scan. The system 3000 may include a CT scanner 2000, one or multiple non-ionizing sensors (not shown in FIG. 3) configured to capture optical imaging data 3001 depicting the patient 1104, a first machine-learning algorithm 3002, a second machine-learning algorithm 3003.

According to the disclosure, the optical imaging data 3001 may be processed by the first (trained) machine-learning algorithm 3002 to generate, for each instance of the optical imaging data 3001, at least one latent vector 3004 representing the corresponding instance of the optical imaging data 3001. A latent vector can generally encode presence or absence of hidden features in the respective instance of the optical imaging data. The type of features can be machine-learned.

Then, the latent vector 3004 is applied to the second (trained) machine-learning algorithm 3003 to generate an initial set of attenuation curves 3005 depicting x-ray attenuation properties of the anatomical target region of the patient 1104 to be scanned by the CT scanner 2000. I.e., the latent vector 3004 serves as input to the second machine-learned algorithm. Thereby, an initial set of the CT scan parameters 3006 is determined based on the initial set of attenuation curves 3005 and thereby used to control elements of the scanner 2000 to start the CT scan.

According to other examples, the latent vector 3004 may be applied to the second (trained) machine-learning algorithm 3003 to directly generate the initial set of the CT scan parameters 3006, i.e., without generating the initial set of attenuation curves 3005.

During the CT scan, the set of attenuation curves 3005 may be updated based on CT imaging data 3007 obtained from the CT scanner 2000 and thereby a new set of the CT scan parameters 3006 is determined based on the updated attenuation curves 3005. Then, the elements of the CT scanner 2000 are controlled based on the new set of the CT scan parameters 3006 to continue to perform the CT scan.

Alternatively, the CT scan parameters 3006 may be directly updated, by the second (trained) machine-learning algorithm 3003, based on the CT imaging data 3007 without intermediately updating the set of attenuation curves 3005.

According to the disclosure, the CT imaging data 3007 may include at least one of sinograms, reconstructed CT images in frequency domain, reconstructed CT images in spatial domain and etc. The CT imaging data 3007 may be 1-D data obtained directly from the detector array 2001, 2-D reconstructed images, or 3-D reconstructed slices including multiple voxels. The CT imaging data 3007 may include only one sonogram, one 2-D image, or one 3-D slice obtained currently, such as at time point $t_0$, $t_1$, or $t_n$, i.e., the new set of the CT scan parameters 3006 is determined based on one instance of current CT imaging data 3007. The CT imaging data 3007 may include multiple instances of current CT imaging data 3007. For example, the CT imaging data 3007 may include all accumulated CT imaging data acquired during the scan, e.g., all imaging data acquired from $t_0$ to $t_n$, or several slices of the accumulated CT imaging data during the scan, e.g., imaging data acquired from $t_1$ to $t_n$.

According to the disclosure, the new set of the CT scan parameters 3006 may be determined immediately after acquiring one slice of the CT imaging data 3007, or after acquiring multiple slices, e.g., 2-10 slices.

According to the disclosure, at least one of patient data 3008 including demographics (e.g., age, height, weight, and etc.), physiological parameters (e.g., heart rate, blood pressure, body temperature, serum levels of various stress hormones and immunological functions, and etc.), or anatomical body markers of the patient 1104 may be further utilized, by the first (trained) machine-learning algorithm 3002, to generate the at least one latent vector 3004. Optionally, at least one of the patient data 3008 may be also utilized by the second (trained) machine-learning algorithm 3003 to update the set of attenuation curves 3005 or to directly update the CT scan parameters 3006.

As a general rule, various kinds and types of machine-learning algorithms can be used as the first and second machine-learning algorithms 3002, 3003 and benefit from the techniques described herein. For instance, it would be possible to use a deep neural network, e.g., a convolutional neural network having one or more convolutional layers performing convolutions between the input data and a kernel, to implement both the first and second machine-learning algorithms 3002, 3003. It would also be possible to use a support vector machine, to give just a few examples. Preferably, the first and second machine-learning algorithms 3002, 3003 may include an encoder and a decoder, respectively. Alternatively, the second machine-learning algorithm 3003 may be an auto-decoder, see, e.g., Park, Jeong Joon, et al. "Deepsdf: Learning continuous signed distance functions for shape representation." *Proceedings of the IEEE/CVF Conference on Computer Vision and Pattern* Recognition. 2019. The second machine-learning algorithms may be a regression model, a generative model or a recurrent model.

As a general rule, the CT scan parameters 3006 may be determined based on the set of attenuation curves 3005 in some scenarios and may be also determined directly in other scenarios, e.g., by using a machine-learning algorithm.

For example, the choice of the technique may depend on the availability of training data. For example, when training data associated with attenuation curves are available, the second machine-learning algorithm 3003 may be trained to determine attenuation curves and thereby the CT scan parameters 3006 may be determined based on the set of attenuation curves 3005. On the other hand, when training data associated with CT scan parameters are available, the second machine-learning algorithm 3003 may be trained to determine the CT scan parameters 3006 directly.

According to various examples, a computer-implemented method for determining CT scan parameters is provided. The CT scan parameters are determined by using machine-learning techniques. The CT scan parameters are used to control elements of a CT scanner to perform a CT scan of an anatomical target region of a patient. The method may include determining, by using at least one machine-learning algorithm and based on optical imaging data depicting the patient, an initial set of the CT scan parameters. The method may further include performing the CT scan starting with the initial set of the CT scan parameters. During the CT scan, the method may optionally include updating the CT scan parameters by using the at least one machine-learning algorithm and based on at least one instance of current CT imaging data obtained from the CT scanner.

In present clinical practices, topograms are usually used to estimate the patient body size, x-ray attenuation properties related to the patient body and thereby determine the CT scan parameters or protocol. Therefore, it may be readily possible to obtain training data associated with attenuation curves. Additionally, training data associated with attenuation curves can include additional information related to an anatomical target region and thereby can facilitate training the at least one machine-learning algorithm to determine the CT scanning parameters more precisely. Thus, techniques related to determining the CT scan parameters based on the set of attenuation curves can have certain benefits.

Hereinafter, techniques are explained where, in an intermediate act, attenuation curves are determined and then, based on the attenuation curves, CT scan parameters are determined. However, it should be understood that it is not necessary in all examples to determine the attenuation curves and the CT scan parameters can be directly determined by using the techniques disclosed in this disclosure. I.e., in this disclosure, corresponding processing acts related to attenuation curves are optional and can be removed.

Figure 4:
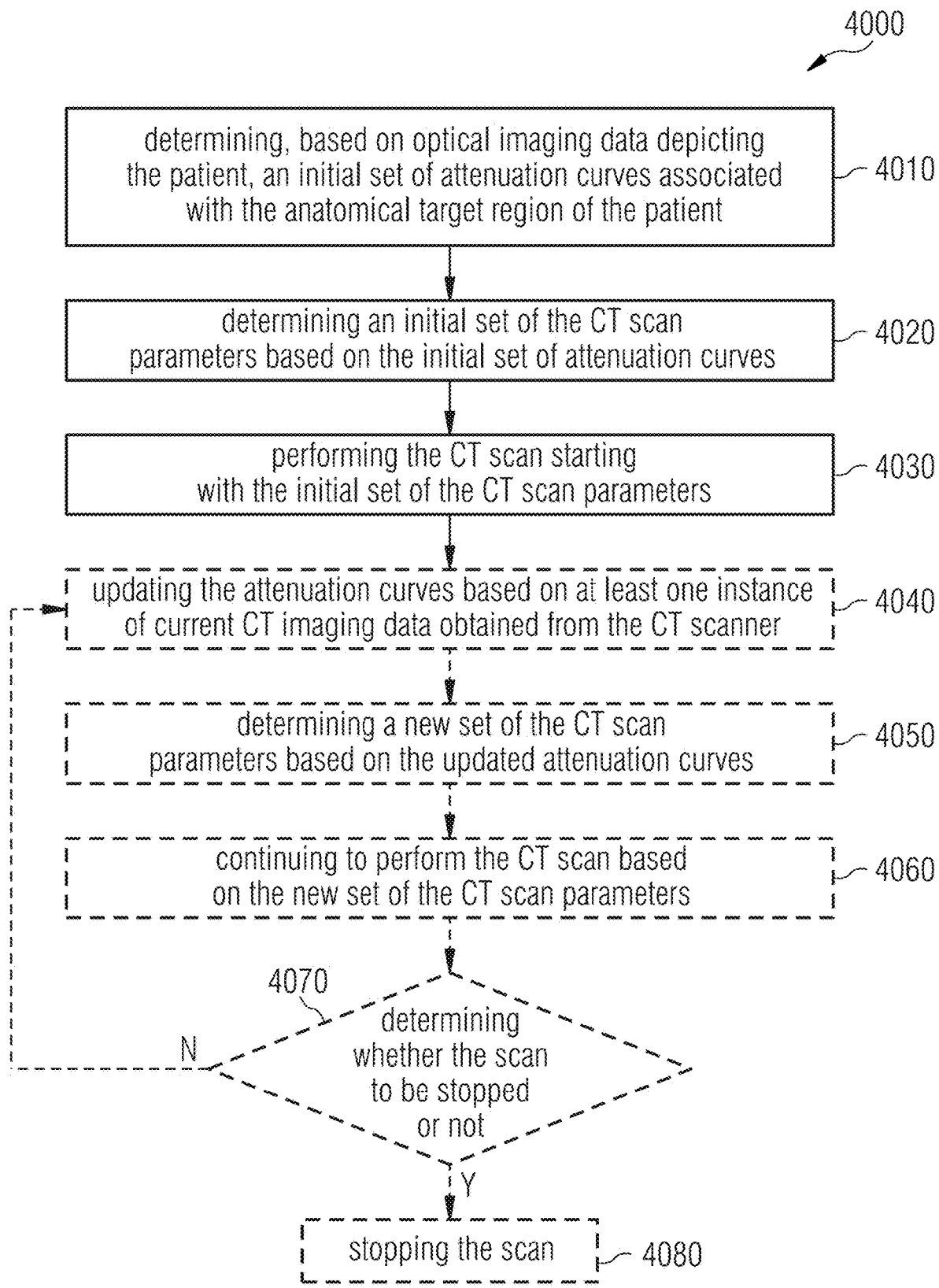
FIG. 4 is a flowchart of a method according to various examples.

FIG. 4 is a flowchart of a method 4000 according to various examples. The method 4000 pertains to determining CT scan parameters 3006 for performing a CT scan of an anatomical target region of a patient 1104, in particular determining an initial set of the CT scan parameters 3006.

Optional blocks are labeled with dashed lines.

The method 4000 may be executed by a computer including at least one processing unit (processor), or by the system 3000 of FIG. 3 upon loading program code. Details of the method 4000 are described below.

At block 4010, an initial set of attenuation curves 3005 associated with the anatomical target region of the patient 1104 is determined based on optical imaging data depicting the patient 1104. For example, 3-D modeling methods, such as digital sculpting, Boolean modeling, laser scanning, box modeling, SubD modeling, or NURBS modeling may be used to determine the initial set of attenuation curves 3005 based on optical imaging data depicting the patient 1104. Alternatively, algorithms for calculating signed distance function, such as efficient fast marching method, fast sweeping method, or level-set method, may be used. Alternatively, or preferably, the first and second trained machine-learning algorithms 3002 and 3003 of FIG. 3 may be used.

Optionally, the initial set of attenuation curves 3005 associated with the anatomical target region of the patient 1104 is determined further based on at least one of demographics, physiological parameters, or anatomical body markers of the patient 1104.

At block 4020, an initial set of the CT scan parameters 3006 is determined based on the initial set of attenuation curves 3005.

At block 4030, the CT scan of the patient 1104 is performed starting with the initial set of the CT scan parameters 3006. For example, elements of the scanner 2000 are respectively controlled based on the initial set of the CT scan parameters 3006 to start the CT scan.

According to the disclosure, an initial set of attenuation curves 3005 associated with the anatomical target region of the patient 1104 may be determined by using the first and second trained machine-learning algorithms 3002 and 3003 of FIG. 3, i.e., an implementation of block 4010, which will be described below.

Figure 5:
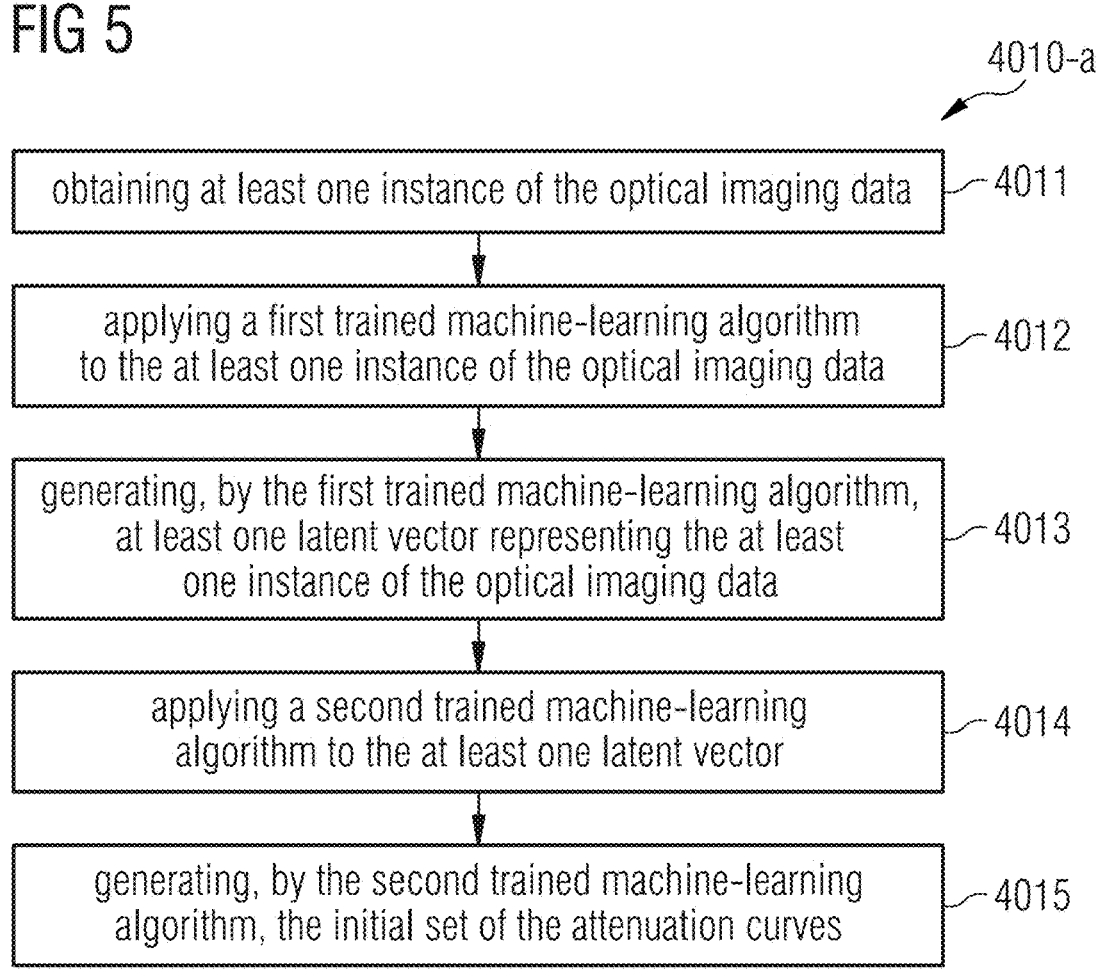
FIG. 5 is a flowchart of a method according to various examples.

FIG. 5 is a flowchart of a method 4010-a according to various examples. The method 4010-a pertains to determining, based on the optical imaging data 3001 depicting the patient 1104, an initial set of attenuation curves 3005 associated with the anatomical target region of the patient 1104 by using the first and second trained machine-learning algorithms 3002 and 3003 of FIG. 3. The method 4010-a is described in further detail below.

At block 4011, at least one instance of the optical imaging data 3001 is obtained, for example by the one or multiple non-ionizing sensors or by retrieving from a database.

At block 4012, the at least one instance of the optical imaging data 3001 is applied to the first trained machine-learning algorithm 3002.

At block 4013, at least one latent vector 3004 representing the at least one instance of the optical imaging data 3001 is generated by the first trained machine-learning algorithm 3002.

At block 4014, the at least one latent vector 3004 is applied to the second trained machine-learning algorithm 3003.

At block 4015, the initial set of the attenuation curves 3005 is generated by the second trained machine-learning algorithm 3003. Alternatively, or optionally, at block 4015, the second trained machine-learning algorithm 3003 may also update values of the at least one latent vector 3004, for example together with generating the initial set of the attenuation curves. The values of the at least one latent vector 3004 may be also updated based on current attenuation curves, i.e., the initial set of the attenuation curves 3005 in this scenario, for example by using Principal Component Analysis (PCA), Independent Component Analysis (ICA), or a trained machine-learning algorithm configured to map the attenuation curves to a set of latent vectors.

Referring to FIG. 4 again, optionally, the method 4000 may further include the following acts until finishing the CT scan at block 4080.

At block 4040, the attenuation curves 3005 are updated based on at least one instance of current CT imaging data 3007 obtained from the CT scanner 2000.

Figure 6:
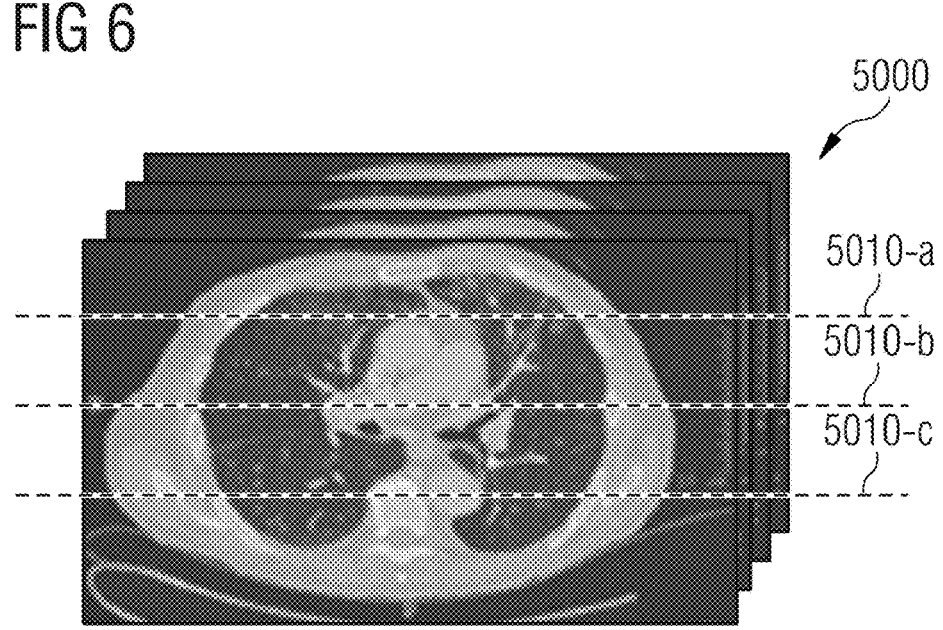
FIG. 6 schematically illustrates exemplary slices of CT images orthogonal to the z-axis.

Further referring to FIG. 6 which schematically illustrates exemplary slices of CT images 5000 in spatial domain and orthogonal to the z-axis, attenuation curves 3005 associated with at least one instance of the CT images 5000 may be respectively determined along lines 5010-a, 5010-b, and 5010-c crossing the CT images 5000 which are parallel with each other and orthogonal to the y-axis. Such attenuation curves may be used to update the attenuation curves 3005. Alternatively, attenuation curves 3005 associated with multiple of the CT images 5000 may be respectively determined along the same lines 5010-a, 5010-b, and 5010-c in each image of the multiple CT images 5000. Then, an average of attenuation curves of the multiple CT images 5000 along the same line may be used to update the attenuation curves 3005. According to various embodiments of the disclosure, the maximum/minimum attenuation curve among attenuation curves of the multiple CT images 5000 along the same line may be used to update the attenuation curves 3005.

Alternatively, the attenuation curves 3005 may be updated by using the second trained machine-learning algorithm 3003 based on an updated latent vector 3004 and at least one instance of the current CT imaging data obtained from the CT scanner, which will be described below in detail with reference to FIG. 7.

According to FIG. 4, at block 4050, a new set of the CT scan parameters 3006 are determined based on the updated attenuation curves 3005.

At block 4060, the CT scan continues to be performed based on the new set of the CT scan parameters 3006.

At block 4070, whether to stop the scan or not is determined. The determination of whether to stop the scan may be based on a comparison between a total number of slices that have been obtained and a predefined total number of slices. If the former is equal to (or larger than) the latter, the scan should be stopped. Such a determination may be also based on a comparison between a total time that has been spent on performing the scan and a predefined total scanning time.

If it is determined to continue the scan, block 4040 will be performed again. Otherwise, block 4080 will be performed to stop the scan.

At block 4080, the scan is stopped.

Figure 7:
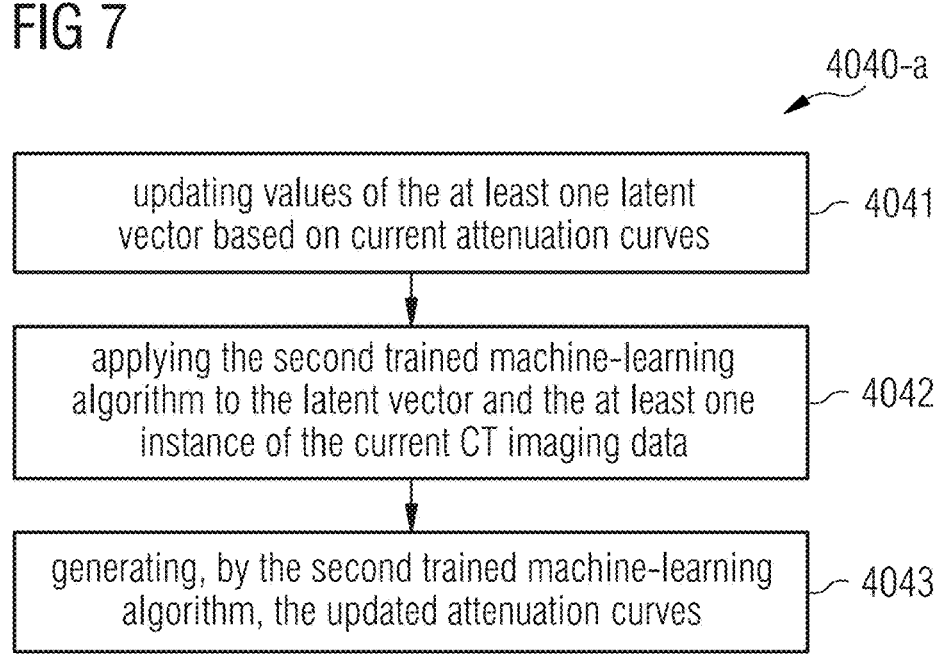
FIG. 7 is a flowchart of a method according to various examples.

FIG. 7 is a flowchart of a method 4040-a according to various examples. The method 4040-a pertains to updating the attenuation curves 3005 based on the latent vector 3004 and at least one instance of the current CT imaging data obtained from the CT scanner, e.g., by the second trained machine-learning algorithm 3003 or by using other methods.

According to the disclosure, the values of the at least one latent vector 3004 may be updated based on current attenuation curves, for example before executing block 4040 of FIG. 4. The values of the at least one latent vector 3004 may be updated by using Principal Component Analysis (PCA), Independent Component Analysis (ICA), or a trained machine-learning algorithm configured to map the attenuation curves to a set of latent vectors.

Alternatively, the values of the at least one latent vector 3004 may be updated by the second trained machine-learning algorithm 3003. For example, the values of the at least one latent vector may be updated in accordance with approaches to optimizing latent vectors as presented by Park, Jeong Joon, et al. ("Deepsdf: Learning continuous signed distance functions for shape representation." *Proceedings of the IEEE/CVF Conference on Computer Vision and Pattern Recognition*. 2019) or by Bojanowski, P., et al. ("Optimizing the latent space of generative networks." *arXiv preprint arXiv*:1707.05776.)

The method 4040-a may include the following aspects.

At block 4041, the values of the at least one latent vector are updated based on current attenuation curves.

At block 4042, the current/updated latent vector 3004 and the at least one instance of the current CT imaging data 3007 are applied to the second trained machine-learning algorithm 3003.

At block 4043, the second trained machine-learning algorithm 3003 generates the updated attenuation curves 3005.

According to the disclosure, the initial set of the CT scan parameters is determined based on optical imaging data, but not based on topograms; and thereby patient radiations caused by acquiring topograms prior to CT scan are eliminated. In addition, the CT scan parameters are automatically and precisely determined/adjusted in real-time based on CT imaging data obtained from the CT scanner during the CT scan or together with updated (current) latent vectors. Thus, patient radiations are controlled as precisely as possible while imaging qualities are maintained as well as possible. Thereby, the patient radiations may be further reduced.

Figure 8:
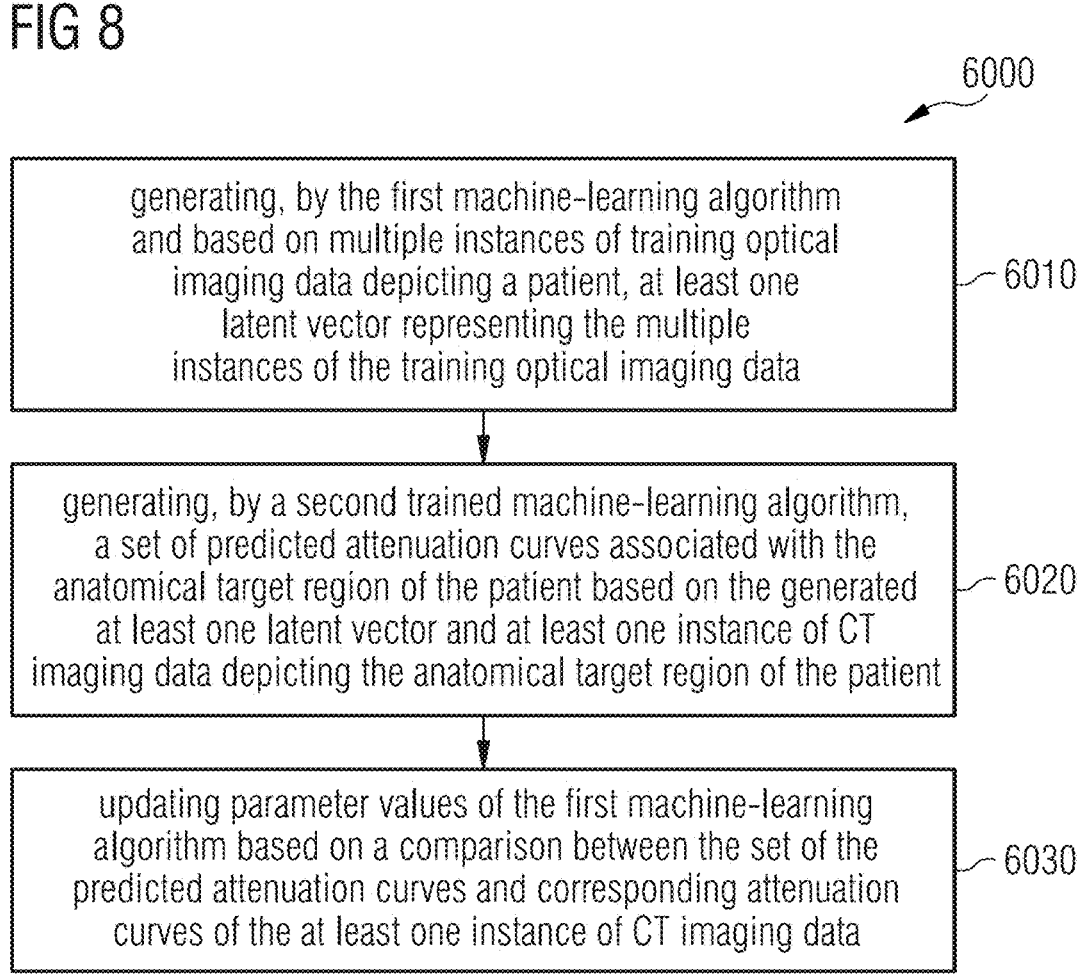
FIG. 8 is a flowchart of a method according to various examples.

FIG. 8 is a flowchart of a method 6000 according to various examples. The method 6000 pertains to performing a first training of the first machine-learning algorithm 3002 for determining CT scan parameters 3006 for performing a CT scan of an anatomical target region. The method 6000 may include the following aspects.

At block 6010, the first machine-learning algorithm 3002 generates at least one latent vector 3004 representing multiple instances of training optical imaging data depicting a patient based on the multiple instances of the training optical imaging data.

According to the disclosure, the first machine-learning algorithm 3002 may firstly obtain the multiple instances of the training optical imaging data depicting the patient by accessing a memory or a database. Then, the first machine-learning algorithm 3002 may be applied to the multiple instances of the training optical imaging data. Thereby, the first machine-learning algorithm 3002 may generate the at least one latent vector representing the multiple instances of the training optical imaging data.

As a general rule, the multiple instances of the training optical imaging data may be associated with multiple patients but depicting the same part of human bodies including the same anatomical target region, such as legs, arms, heads, chests, abdomens, etc. The training optical imaging data may share the same characteristics as the optical imaging data described above.

Optionally, the at least one latent vector 3004 representing the multiple instances of the training optical imaging data is generated further based on at least one of demographics, physiological parameters, or anatomical body markers of the patient. Such additional data associated with the patient may facilitate a more accurate generation of the at least one latent vector 3004.

At block 6020, the second trained machine-learning algorithm 3003 generates a set of predicted attenuation curves associated with the anatomical target region of the patient based on the generated at least one latent vector and at least one instance of CT imaging data depicting the anatomical target region of the patient.

According to the disclosure, the second trained machine-learning algorithm 3003 may firstly obtain the at least one instance of CT imaging data depicting the anatomical target region of the patient by accessing a memory or a database. Then, the second trained machine-learning algorithm 3003 may be applied to the at least one latent vector representing the multiple instances of the training optical imaging data and the at least one instance of CT imaging data, and thereby generate the set of the predicted attenuation curves.

At block 6030, parameter values of the first machine-learning algorithm 3003 are updated based on a comparison between the set of the predicted attenuation curves and corresponding attenuation curves of the at least one instance of the CT imaging data.

As a general rule, at least one of $L_1$ loss, L2 loss, or Laplacian pyramid loss may be used to update the parameter values of the first machine-learning algorithm 3003.

Optionally, the method 6000 may further include freezing parameter values of the second trained machine-learning algorithm when updating the parameter values of the first machine-learning algorithm.

According to the disclosure, the training of the first machine-learning algorithm 3002 may be performed based on the trained second machine-learning algorithm 3003, i.e., parameter values of the second machine-learning algorithm 3003 may be frozen during the whole training procedure. Using the trained second machine-learning algorithm 3003 to train the first machine-learning algorithm 3002 may facilitate the accuracy of the training and speed up the training.

FIG. 9 is a flowchart of a method 7000 according to various examples. The method 7000 pertains to performing a second training of the second machine-learning algorithm 3003 for determining CT scan parameters for performing a CT scan of an anatomical target region. The method 7000 may include the following aspects.

At block 7010, values of at least one latent vector 3004 are randomly generated.

According to the disclosure, a randomly initialized latent vector may be generated from a predefined probability distribution, such as a Normal distribution with different mean and variance.

At block 7020, at least one instance of CT imaging data depicting the anatomical target region of a patient is obtained, for example by accessing a memory or a database.

At block 7030, the second machine-learning algorithm is applied to the generated at least one latent vector and the at least one instance of CT imaging data.

At block 7040, a set of predicted attenuation curves associated with the anatomical target region of the patient is generated. The predicted attenuation curves may share the same characteristics as the attenuation curves described above.

At block 7050, parameter values of the second machine-learning algorithm 3003 and the values of the at least one latent vector 3004 are jointly updated based on a comparison between the set of the predicted attenuation curves and corresponding attenuation curves of the at least one instance of CT imaging data.

According to the disclosure, the values of the at least one latent vector 3004 may be updated along with the parameter values of the second machine-learning algorithm 3003 through standard backpropagation. During inference, the values of the at least one latent vector may be estimated by the second machine-learning algorithm 3003 by fixing the parameter values thereof.

As a general rule, the techniques for updating the values of the latent vector 3004 explained above may be alternatively applied for training the second machine-learning algorithm 3003.

As a further general rule, at least one of $L_1$ loss, $L_2$ loss, or Laplacian pyramid loss may be used to update the parameter values of the second machine-learning algorithm 3005.

Optionally or preferably, blocks 7010-7050 of the method 7000 may be reiterated based on multiple instances of CT imaging data of further patients depicting the anatomical target region to increase training accuracy. I.e., the method 7000 may further include obtaining at least one further instance of CT imaging data of a further patient depicting the anatomical target region; applying the second machine-learning algorithm to the at least one latent vector and the at least one further instance of CT imaging data; generating a further set of predicted attenuation curves associated with the anatomical target region of the further patient; jointly updating parameter values of the second machine-learning algorithm and the values of the at least one latent vector based on a comparison between the further set of predicted attenuation curves and corresponding attenuation curves of the at least one further instance of CT imaging data.

FIG. 10 is a block diagram of a system 9000 according to various examples. The system 9000 pertains to training the second machine-learning algorithm 3003 based on the method 7000 and train the first machine-learning algorithm 3002 based on the method 6000.

The system 9000 may include at least one processor 9020, at least one memory 9030, and at least one input/output interface 9010. The at least one processor 9020 is configured to load program code from the at least one memory 9030 and execute the program code. Upon executing the program code, the at least one processor 9020 performs the method 6000 and the method 7000 of performing the first and second training of the first and second machine-learning algorithms, respectively.

Referring to FIG. 2 again, the CT scanner 2000 may further include at least one optical imaging device configured to capture optical imaging data depicting a patient and a computing unit configured to perform the methods 4000, 4010-a, or 4040-a.

Alternatively, the system 9000 may be embedded in or connected with the CT scanner 2000 and thereby the CT scanner 2000 may be also configured to perform the methods 6000 and/or 7000.

Summarizing, techniques have been described that facilitate determining CT scan parameters and thereby controlling elements of a CT scanner to perform a scan. Optical imaging data depicting patients may be used to replace topograms for determining an initial set of CT scan parameters and initializing the elements of the CT scanner. During the CT scan, acquired CT imaging data may be used to further automatically and in real-time determine/adjust CT scan parameters and thereby control the elements of the CT scanner to continue the scan. Additionally, latent vectors representing an anatomical target region of a patient may be also updated based on the acquired CT imaging data to facilitate the accuracy of the determination of the CT scan parameters. Thus, patient radiations are controlled as precisely as possible while imaging qualities are maintained as well as possible. Thereby, the patient radiations may be precisely reduced.

Although the disclosure has been shown and described with respect to certain preferred embodiments, equivalents and modifications will occur to others skilled in the art upon the reading and understanding of the specification. The present disclosure includes all such equivalents and modifications and is limited only by the scope of the appended claims.

We claim:

1. A computer-implemented method for determining computed tomography (CT) scan parameters for performing a CT scan of an anatomical target region of a patient, the method comprising:
    determining, based on optical imaging data depicting the patient, an initial set of attenuation curves associated with the anatomical target region of the patient, wherein said determining of the initial set of attenuation curves associated with the anatomical target region of the patient comprises:
    obtaining at least one instance of the optical imaging data;
    applying a first trained machine-learning algorithm to the at least one instance of the optical imaging data;
    generating, by the first trained machine-learning algorithm, at least one latent vector representing the at least one instance of the optical imaging data;
    applying a second trained machine-learning algorithm to the at least one latent vector; and
    generating, by the second trained machine-learning algorithm, the initial set of the attenuation curves;
    determining an initial set of the CT scan parameters based on the initial set of attenuation curves; and
    performing the CT scan starting with the initial set of the CT scan parameters.

2. The computer-implemented method of claim 1, further comprising iteratively performing the following acts during the CT scan:
    updating the attenuation curves based on at least one instance of current CT imaging data obtained from a CT scanner;
    determining a new set of the CT scan parameters based on the updated attenuation curves; and
    continuing to perform the CT scan based on the new set of the CT scan parameters.

3. The computer-implemented method of claim 2, wherein the method further comprises:
    updating values of the at least one latent vector based on current attenuation curves;
    wherein said updating of the attenuation curves based on the at least one instance of the current CT imaging data obtained from the CT scanner comprises:
    applying the second trained machine-learning algorithm to the latent vector and the at least one instance of the current CT imaging data; and
    generating, by the second trained machine-learning algorithm, the updated attenuation curves.

4. The computer-implemented method of claim 1, wherein the CT scan parameters comprise at least one of scan range, detector configuration, tube current, tube potential, patient positioning, reconstructed slice thickness, or pitch.

5. The computer-implemented method of claim 1, wherein said determining the initial set of attenuation curves associated with the anatomical target region of the patient is further based on at least one of demographics, physiological parameters, or anatomical body markers of the patient.

6. The computer-implemented method of claim 1, wherein the first trained machine-learning algorithm comprises an encoder and the second trained machine-learning algorithm comprises a decoder.

7. A computer-implemented method of performing a first training of a first machine-learning algorithm for determining computed tomography (CT) scan parameters for performing a CT scan of an anatomical target region, the method comprising:
   generating, by the first machine-learning algorithm and based on multiple instances of training optical imaging data depicting a patient, at least one latent vector representing the multiple instances of the training optical imaging data;
   generating, by a second trained machine-learning algorithm, a set of predicted attenuation curves associated with the anatomical target region of the patient based on the generated at least one latent vector and at least one instance of CT imaging data depicting the anatomical target region of the patient; and
   updating parameter values of the first machine-learning algorithm based on a comparison between the set of the predicted attenuation curves and corresponding attenuation curves of the at least one instance of CT imaging data.

8. The computer-implemented method of claim 7, further comprising:
   freezing parameter values of the second trained machine-learning algorithm when updating the parameter values of the first machine-learning algorithm.

9. The computer-implemented method of claim 7, wherein said generating the at least one latent vector representing the multiple instances of the training optical imaging data comprises:
   obtaining the multiple instances of the training optical imaging data depicting the patient;
   applying the first machine-learning algorithm to the multiple instances of the training optical imaging data; and
   generating, by the first machine-learning algorithm, the at least one latent vector representing the multiple instances of the training optical imaging data.

10. The computer-implemented method of claim 7, wherein said generating the set of the predicted attenuation curves comprises:
   obtaining the at least one instance of CT imaging data depicting the anatomical target region of the patient;
   applying the second trained machine-learning algorithm to the at least one latent vector representing the multiple instances of the training optical imaging data and the at least one instance of CT imaging data; and
   generating, by the second trained machine-learning algorithm, the set of the predicted attenuation curves.

11. The computer-implemented method of claim 7, wherein said generating the at least one latent vector representing the multiple instances of the training optical imaging data is further based on at least one of demographics, physiological parameters, or anatomical body markers of the patient.

12. A computer-implemented method of performing a second training of a second machine-learning algorithm for determining computed tomography (CT) scan parameters for performing a CT scan of an anatomical target region, the method comprising:
   randomly generating values of at least one latent vector;
   obtaining at least one instance of CT imaging data depicting the anatomical target region of a patient;
   applying the second machine-learning algorithm to the generated at least one latent vector and the at least one instance of CT imaging data;
   generating a set of predicted attenuation curves associated with the anatomical target region of the patient; and
   jointly updating parameter values of the second machine-learning algorithm and the values of the at least one latent vector based on a comparison between the set of the predicted attenuation curves and corresponding attenuation curves of the at least one instance of CT imaging data.

13. The computer-implemented method of claim 12, further comprising iteratively performing the following acts:
   obtaining at least one further instance of CT imaging data of a further patient depicting the anatomical target region;
   applying the second machine-learning algorithm to the at least one latent vector and the at least one further instance of CT imaging data;
   generating a further set of predicted attenuation curves associated with the anatomical target region of the further patient; and
   jointly updating parameter values of the second machine-learning algorithm and the values of the at least one latent vector based on a comparison between the further set of predicted attenuation curves and corresponding attenuation curves of the at least one further instance of CT imaging data.

14. A computed tomography (CT) scanner comprising:
   at least one optical imaging device configured to capture optical imaging data depicting a patient; and
   a computer configured to:
      determine, based on the optical imaging data depicting the patient, an initial set of attenuation curves associated with an anatomical target region of the patient, wherein, to determine the initial set of attenuation curves, the computer is configured to:
         obtain at least one instance of the optical imaging data;
         apply a first trained machine-learning algorithm to the at least one instance of the optical imaging data;
         generate, by the first trained machine-learning algorithm, at least one latent vector representing the at least one instance of the optical imaging data;
         apply a second trained machine-learning algorithm to the at least one latent vector; and
         generate, by the second trained machine-learning algorithm the initial set of the attenuation curves;
      determine an initial set of CT scan parameters based on the initial set of attenuation curves; and
      perform the CT scan starting with the initial set of the CT scan parameters.

15. The CT scanner of claim 14, wherein the computer is further configured to iteratively perform during the CT scan:

update the attenuation curves based on at least one instance of current CT imaging data obtained from a CT scanner;

determine a new set of the CT scan parameters based on the updated attenuation curves; and continue to perform the CT scan based on the new set of the CT scan parameters.

16. The CT scanner of claim 15, wherein the computer is configured to:

update values of the at least one latent vector based on current attenuation curves, wherein the update of the attenuation curves based on the at least one instance of the current CT imaging data obtained from the CT scanner comprises application of the second trained machine-learning algorithm to the latent vector and the at least one instance of the current CT imaging data and generate, by the second trained machine-learning algorithm, the updated attenuation curves.

17. The CT scanner of claim 14, wherein the CT scan parameters comprise at least one of scan range, detector configuration, tube current, tube potential, patient positioning, reconstructed slice thickness, or pitch and wherein the first trained machine-learning algorithm comprises an encoder and the second trained machine-learning algorithm comprises a decoder.

18. The CT scanner of claim 14, wherein the computer is configured to determine the initial set of attenuation curves associated with the anatomical target region of the patient based on at least one of demographics, physiological parameters, or anatomical body markers of the patient.

* * * * *